(12) United States Patent
Kim

(10) Patent No.: US 9,341,867 B1
(45) Date of Patent: May 17, 2016

(54) METHODS OF DESIGNING AND FABRICATING CUSTOM-FIT EYEGLASSES USING A 3D PRINTER

(71) Applicant: James Chang Ho Kim, Woodside, NY (US)

(72) Inventor: James Chang Ho Kim, Woodside, NY (US)

(*) Notice: Subject to any disclaimer, the term of this patent is extended or adjusted under 35 U.S.C. 154(b) by 0 days.

(21) Appl. No.: 14/598,270

(22) Filed: Jan. 16, 2015

(51) Int. Cl.
*A61B 3/04* (2006.01)
*G02C 13/00* (2006.01)
*A61B 3/11* (2006.01)
*G02C 7/02* (2006.01)
*B33Y 50/00* (2015.01)
*B33Y 10/00* (2015.01)
*B33Y 30/00* (2015.01)
*B33Y 80/00* (2015.01)

(52) U.S. Cl.
CPC ............ *G02C 13/005* (2013.01); *A61B 3/111* (2013.01); *G02C 7/027* (2013.01); *B33Y 10/00* (2014.12); *B33Y 30/00* (2014.12); *B33Y 50/00* (2014.12); *B33Y 80/00* (2014.12); *G02C 2200/14* (2013.01); *G02C 2202/16* (2013.01)

(58) Field of Classification Search
USPC ......................................... 351/204, 227, 178
See application file for complete search history.

(56) References Cited

U.S. PATENT DOCUMENTS

| | | | |
|---|---|---|---|
| 2,663,949 A | 8/1948 | Huston | |
| 5,592,248 A | 1/1997 | Norton et al. | |
| 6,095,650 A | 8/2000 | Gao et al. | |
| 6,231,188 B1 | 5/2001 | Gao et al. | |
| 6,508,553 B2 | 1/2003 | Gao et al. | |
| 6,634,754 B2 | 10/2003 | Fukuma et al. | |
| 6,682,195 B2 | 1/2004 | Dreher | |
| 6,692,127 B2 | 2/2004 | Abitbol et al. | |
| 6,944,327 B1 | 9/2005 | Soatto | |
| 7,291,002 B2 | 11/2007 | Russell et al. | |
| 7,292,713 B2 | 11/2007 | Fukuma et al. | |
| 7,597,835 B2 | 10/2009 | Marsac | |
| 7,665,843 B2 | 2/2010 | Xie | |
| 7,959,287 B1 | 6/2011 | Saffra | |
| 8,220,923 B2 | 7/2012 | Saffra | |
| 8,708,494 B1 | 4/2014 | Surkov et al. | |
| 8,733,936 B1 | 5/2014 | Kornilov et al. | |
| 8,838,263 B2 | 9/2014 | Sivak et al. | |
| 2014/0257839 A1 | 9/2014 | Suter et al. | |

*Primary Examiner* — Jack Dinh
(74) *Attorney, Agent, or Firm* — Michael J. Feigin, Esq.; Feigin & Fridman

(57) ABSTRACT

The disclosed technology describes methods for the selection, design and production of custom-fit eyeglasses, using a 3D printer. Embodiments include an eye examination and biometric measurements of a patient. The data can be used to produce custom-fit eyeglass frames. Eyeglass selection is facilitated by the display of a selection of various frames in both digital and physical form. A 3D version of the patient's head may be created from digital images, which can be used to produce a final version of the eyeglass frame. Lens dimensions may be traced and the trace used to modify the eyeglass frame. Half of an eyeglass frame may be generated, from which a mirror image is created, and a final frame produced from the resulting image. Also disclosed is an electronic device system which receives, processes and transmits data for the production of custom-fit eyeglass frames.

19 Claims, 9 Drawing Sheets

METHODS OF DESIGNING AND FABRICATING CUSTOM-FIT EYEGLASSES USING A 3D PRINTER

FIELD OF THE DISCLOSED TECHNOLOGY

The disclosed technology relates generally to fabrication of custom fit eyeglasses using a three dimensional printer.

BACKGROUND OF THE DISCLOSED TECHNOLOGY

Even with the advent of contact lenses and Lasik surgery, eyeglasses are still a common means to correct vision. Choosing the most suitable eyeglass frame in both style and fit is a daunting task, considering the wide variety of eyeglass frames produced by a multitude of manufacturers. The uniqueness in the size and shape of each individual's head further complicates the process of selecting and fitting an eyeglass frame to a particular individual. Once an eyeglass frame is selected, the impediment to the expeditious delivery of eyeglasses to the customer is the delay caused during the manufacturing process. What is needed is a method that enhances efficiency in the eyeglass selection process, as well as precision in fitting the eyeglass to satisfy the wearer's aesthetic requirements, while achieving superior comfort and performance; and speed in the fabrication of the eyeglasses.

SUMMARY OF THE DISCLOSED TECHNOLOGY

The methods in the disclosed technology meet the needs existing in the prior art in a number of ways. First, eyeglass selection is facilitated by the display of an extensive selection of multiple eyeglass frames in both digital and physical form, constituting a plurality of eyeglass frame sizes, styles, designs, composition, and colors. The terms eyeglasses, eyeglass frame, and frame are used interchangeably in this application. An eye examination of the patient and biometric measurements of the patient are conducted at the office of an eye care professional. These data are used alone or with additional data, such as preliminary lens and frame specifications, to produce custom-fit eyeglass frames by means of a three-dimensional printer.

In an embodiment of the technology, a patient eye examination is conducted to determine the patient's optical specifications for vision correction. This may include two of the following: eye strength, refractive error, sphere, cylinder, axis and prism. Biometric data of the patient's head are also collected and may include two of the following measurements: distance between the patient's pupils, frontal curvature of patient's skull from temple to temple, distance from the front of the patient's temples to the back of the ear, and dimensions and shape of patient's eyes and bridge of the nose. An eyeglass frame is chosen from a plurality of eyeglass frames, each of which represents a different style, wherein style is defined as having a specific thickness between the top of the frame and lens opening, left and right arms, a distinct bridge for a nose, and a distinct lens opening width or height. A determination is made of lens dimensions which match the dimensions of the selected eyeglass frame. The eyeglass frame is then printed layer by layer with a three dimensional printer after modifying the shape of at least two features of the frame, using the patient's biometric data, a color of at least a part of the frame, and adding at least one design to said frame.

In a further embodiment, the hinges between the left and/or right arms of the selected frame to match the printed eyeglass frame dimensions and printing such a modified hinge. An "arm," as used in this application, is defined as an eyeglass "temple".

The plurality of eyeglass frames may comprise a combination of physical frames and digital images, wherein the frames may be modified in shape.

Also disclosed is the process of acquiring a series of digital images of a patient's head, comprising images of at least the face and sides of the head, and modifying the shape of at least two different portions of the selected frame based on a superimposition of the said frame on the said digital images.

Another embodiment includes the creation of a three-dimensional version of said patient's head from a series of digital images, using said biometric data.

The disclosed technology also includes a method in which the left and right arms of the selected eyeglass frame are generated by form-fitting two curves and combining them, wherein one of the curves is sized using the shape and size of one of the left and right arms, and the second of the curves having the shape of one of the patient's temples, based on the patient's biometric data and the three-dimensional version of the patient's head.

Also disclosed is a method wherein a single outline of a lens is traced, and the dimensions of such a lens are used to modify the shape of the selected eyeglass frame.

A further embodiment is a method, wherein the specification upon which the eyeglass frame is printed further comprises the traced outline of the lens.

In another embodiment of the disclosed technology, a preliminary lens outline is created based on the biometric data and the optical specifications of a user. The preliminary lens outline is digitally shaped in a preliminary eyeglass frame design to achieve a final lens design and the preliminary eyeglass frame design having at least a distinct thickness between a top of the frame and a lens opening and a distinct lens opening width or height. A half frame of the preliminary eyeglass frame is generated, which, in turn, is used to produce a mirror image of the half frame. The preliminary eyeglass frame can be modified and shaped using a final lens design, the half frame and mirror image of the half frame, to create a final frame design. A nose piece is molded using the patient biometric data and final frame design. Said final frame design is modified and the nose piece is printed layer by layer, using a three-dimensional printer, after modifying a color of at least a part of the final frame design and adding at least one design to the final frame design.

Another embodiment includes the above-described method, wherein the final frame design includes left and right arms, and the left and right arms are generated using said patient biometric data.

Also disclosed is a method, wherein the left and right arms of the final frame design are separated, and using a liquid resin printer to print three-dimensional replicas of the final frame design and the left and right arms to scale.

A further embodiment is a method wherein the biometric data and the optical specifications are used to generate a second lens for assembly into the final frame design.

Another embodiment of the disclosed technology is the method of modifying the final frame, using the patient's frontal facial curvature.

The disclosure also includes the method of modifying the shape of hinges between the left and/or right arms of the final design to match the printed final frame design.

The disclosed technology also includes a system with a processor (a device which carries out instructions), an input mechanism for transmitting the data and information to the processor, and a three-dimensional printer functionally connected to the processor for printing a custom fit and designed eyeglass frame. These devices work to carry out the fabrication of a custom fit (specific size to fit the wearer) and designed (specific look based on wearer's aesthetic requests) eyeglass frame, using data retrieved. The data and information can include the patient's eye examination data, the patient's biometric data, and preliminary eyeglass frame size data, wherein a preliminary eyeglass frame design includes a frame portion defining two lens receiving openings the frame portion further supporting left and right arms, the arms located on opposite distal ends of the frame portion, and wherein the preliminary eyeglass frame size data includes lens opening width and height, bridge width, temple length and total widt. After receiving the data and information, the processor implements a fit analysis, using the preliminary eyeglass frame design size data, the biometric data, and the optical specifications to alter the preliminary eyeglass frame design to generate a custom-fit eyeglass frame for the patient. Said custom-fit eyeglass frame is then printed layer by layer, using the three-dimensional printer.

A further embodiment includes a system, wherein the processor executes instructions for generating an outline of a preliminary lens, using the patent biometric data and the optical specifications; the processor further implements instructions that determine the vertical and outward shape of the outline of the preliminary lens in the preliminary eyeglass frame design.

Further disclosed is a system wherein the processor executes instructions for generating a one-half bridge portion of the preliminary eyeglass frame design, a mirror image of the one-half nose bridge portion, and a mirror image of the preliminary eyeglass frame design, wherein the processor uses the patient biometric data, the optical specifications and the preliminary eyeglass frame size data to generate a final eyeglass frame design, a final lens design, and a final nose bridge design.

In another embodiment, the processor uses the final eyeglass frame design and the patient biometric data to mold a nose piece for the final eyeglass frame design.

The disclosed technology includes a method wherein the nose piece is printed layer by layer, using the three-dimensional printer, and the nose piece is assembled onto the final eyeglass frame design after printing.

The technology permits custom fit eyeglasses to be produced instantaneously during the patient's initial office visit, thus eliminating the delay in fabricating the eyeglasses off-site. Even if eyeglasses are prepared at the eye professional's office, typically the manufacture of the eyeglasses cannot be carried out immediately, so that the patient must return at a later time to receive the eyeglasses and have them fitted. The advantage of the subject technology is that the eyeglasses can be worn and evaluated immediately for proper fit, after production during the initial office visit, so as to avoid the time and expense of a second visit to receive and fit the eyeglasses.

"Substantially" and "substantially shown," for purposes of this specification, are defined as "at least 90%," or as otherwise indicated. Any device may "comprise" or "consist of" the devices mentioned there-in, as limited by the claims.

It should be understood that the use of "and/or" is defined inclusively such that the term "a and/or b" should be read to include the sets: "a and b," "a or b," "a," "b."

DETAILED DESCRIPTION OF EMBODIMENTS OF THE DISCLOSED TECHNOLOGY

The disclosed technology described herein sets forth methods of designing and producing a custom fit eyeglass frame, based on the results of an eye examination and biometric data, using a three-dimensional printer to print glasses after modifying their shape and style, as desired by a patient. Further, an eyeglass lens can be traced (defined as drawing the exterior contours of the generally flat elongated side by way of manual and/or computer aided creation of same) to modify or limit modifications to the shape of desired eyeglass frames.

Embodiments of the disclosed technology will become clearer in view of the following discussion of the figures.

Figure 1:
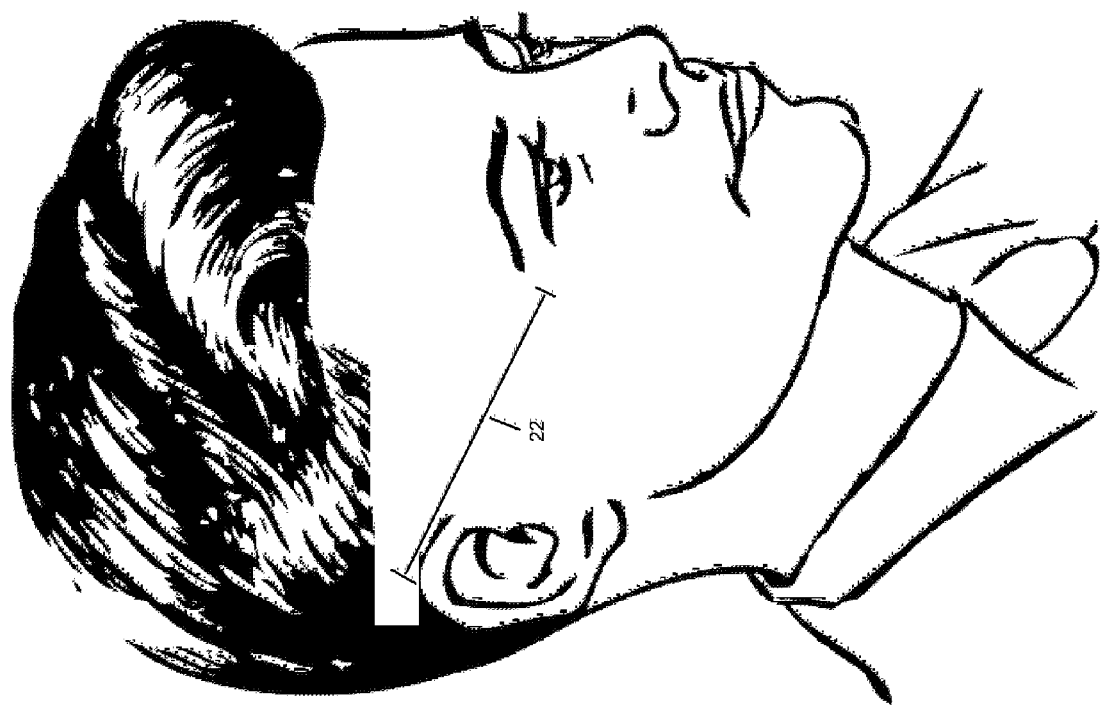
FIG. 1 shows a front elevation of a face depicting biometric measurements.
Figure 2:
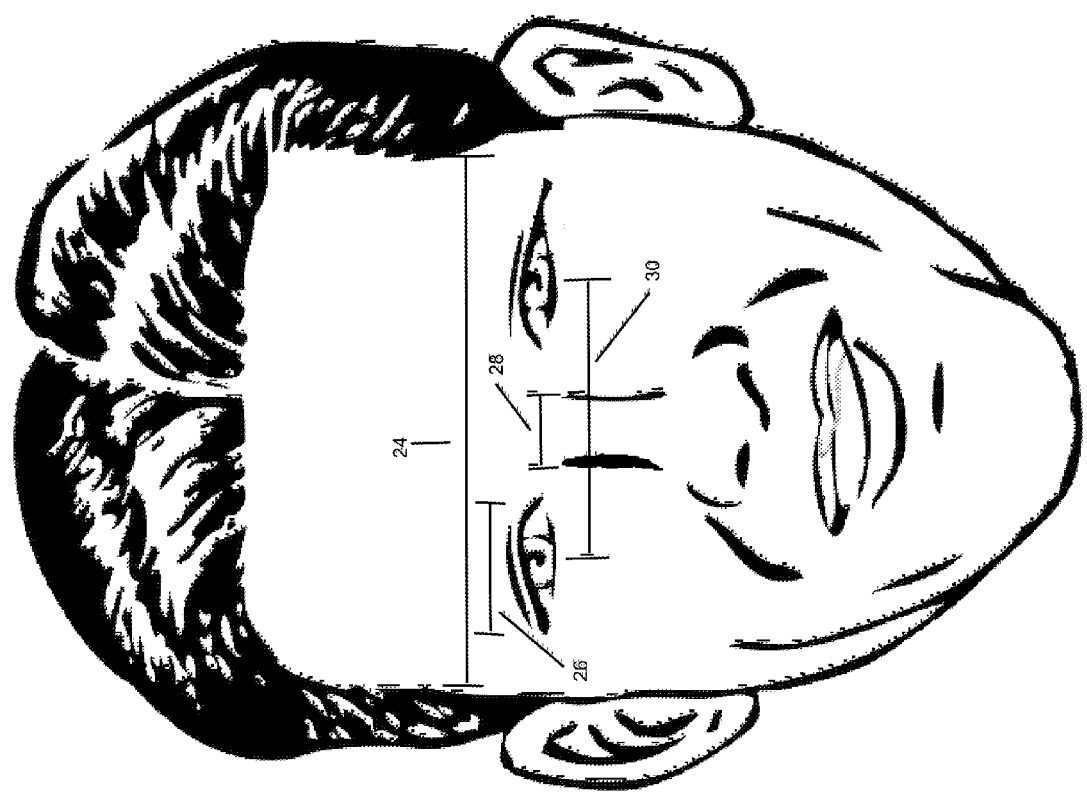
FIG. 2 shows a side elevation view of a head showing biometric measurement to be performed.
Figure 3:
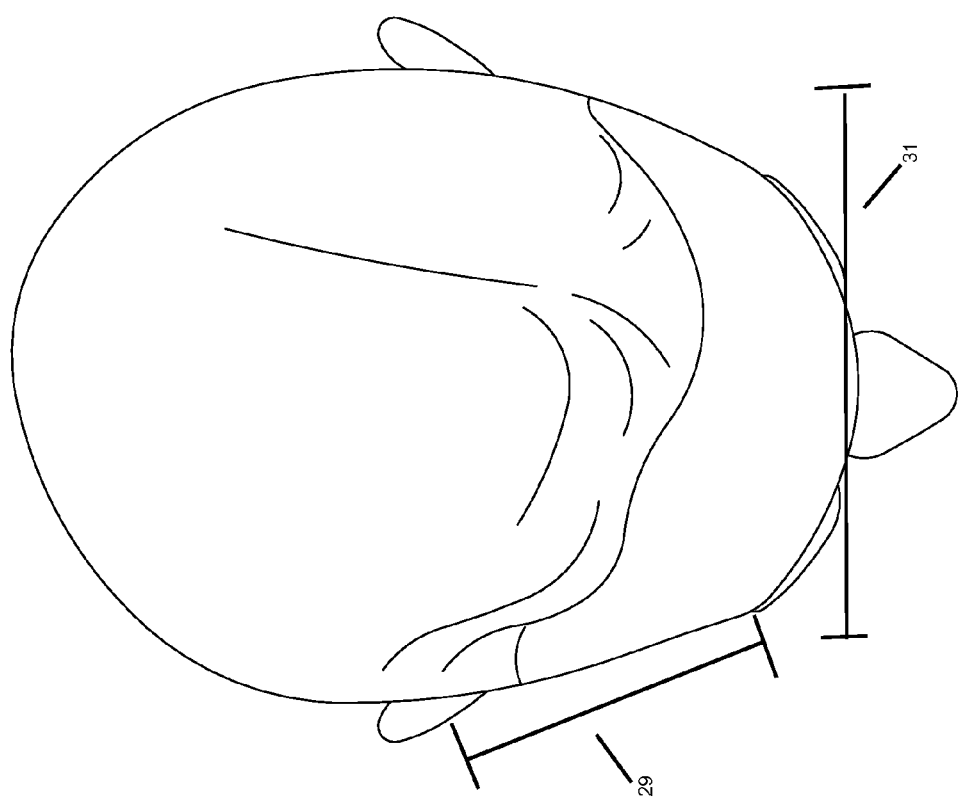
FIG. 3 shows a top view of a head showing the temple curvature and facial curvature biometric measurements to be performed.
Figure 4:
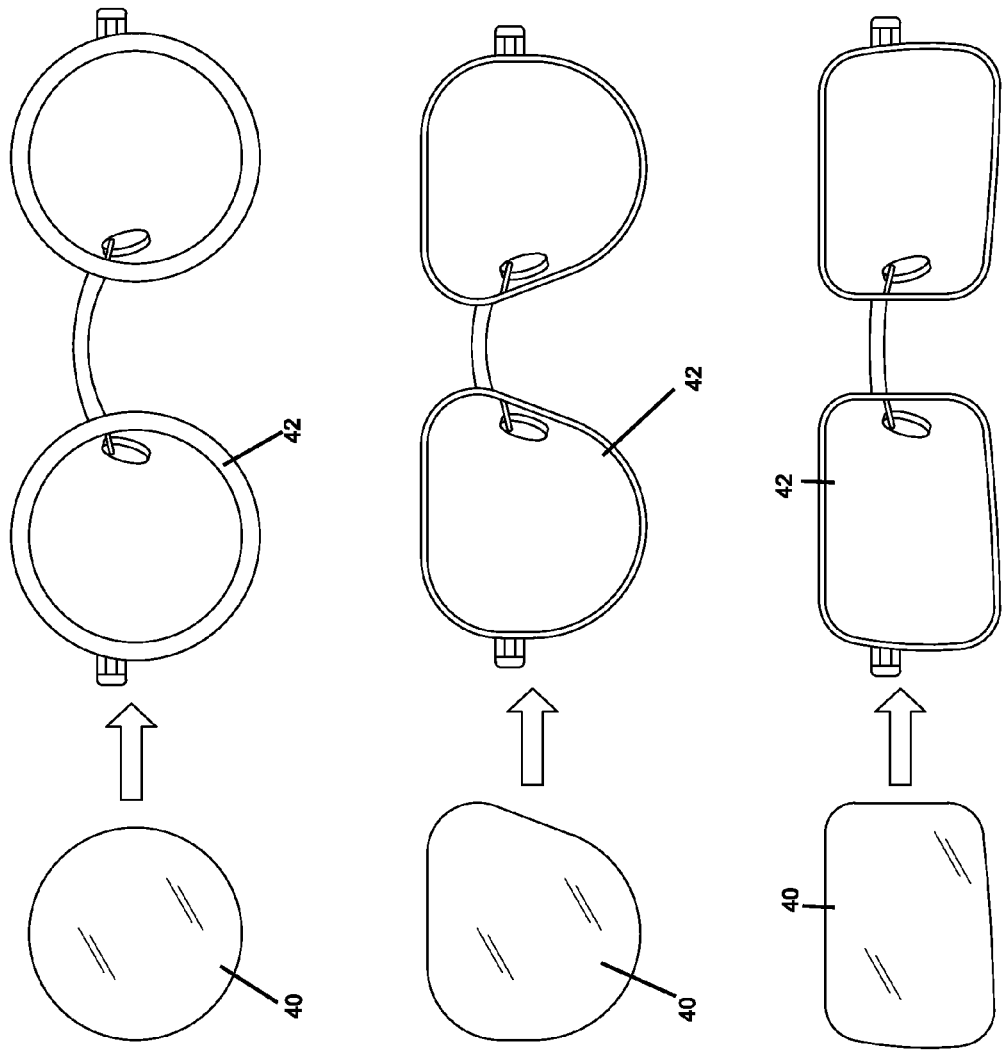
FIG. 4 shows the process of using lens dimensions to modify a frame to conform to such dimensions.
Figure 5:
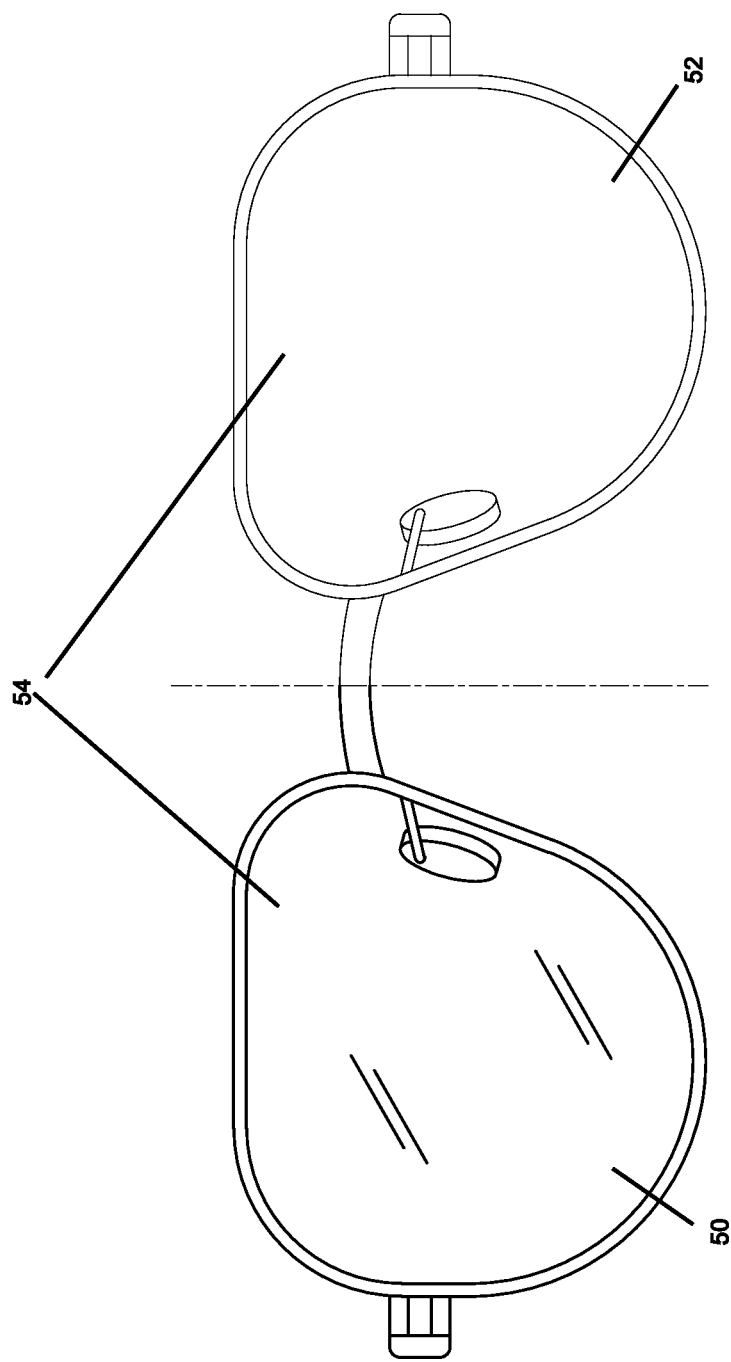
FIG. 5 shows the process of generating a half frame mirror image from an original half frame.

FIG. 1 depicts a biometric measurement that may be taken in embodiments of the disclosed technology, including from the front of the temple to the rear of a patient's ear, where the ear attaches to the head 22. FIG. 2 depicts further biometric measurements that may be taken including: from a first to a second temple 24, width of an eye 26, width of the bridge of the nose, and distance between the pupils 30. FIG. 3 depicts still further biometric measurements that may be taken, including the curvature of the temple from the front of the temple to the rear of a patient's ear, where the ear attaches to the head 29 and the curvature of the front of a patient's head from a first temple to a second temple 31. FIG. 4 depicts the process of using a lens of specific dimensions and shape 40 to modify an eyeglass frame 42, to match the dimensions and shape of the lens. FIG. 5 depicts the process of creating a half of a nose bridge and frame 50 and generating a mirror image of said half nose bridge and frame 52, to produce a complete version of an eyeglass frame 54.

Figure 6:
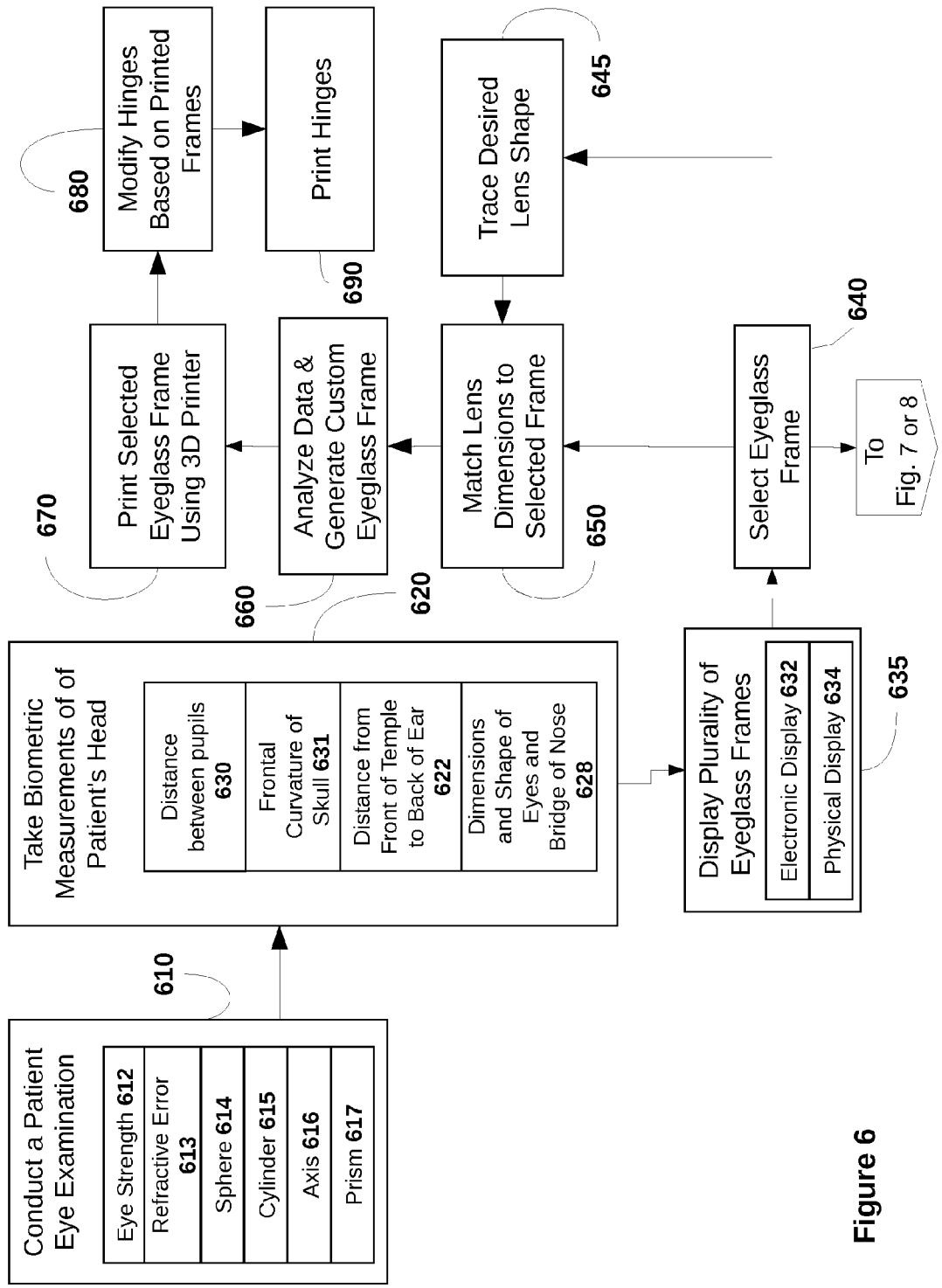
FIG. 6 shows a flowchart depicting the process of constructing eyeglass frames using a three dimensional printer based on the results of an eye examination and, alternatively, with the additional steps of tracing a lens which fits the shape of a selected eyeglass frame and modifying the shape of the eyeglass frame based on the traced lens.

FIG. 6 shows a flowchart depicting the process of constructing eyeglass frames, using a three-dimensional printer, based on the results of an eye examination. In a first step, a patient eye examination is conducted. This eye examination, in embodiments of the disclosed technology, can include various measurements, such as measurement of eye strength 612. Measurement of eye strength is defined as an assessment of the patient's eyes to focus light rays on the retina and visualize a clear image. Refractive error 613 can be measured, which is defined as the ability to focus parallel light rays emanating from distant objects on the retina. Sphere 614 is also measured in embodiments of the technology. Sphere is defined as the amount of lens power, measured in diopters, necessary to correct errors in vision. In turn, diopter is defined as the measure of the refractive power of an optical system. Cylinder 615 can be measured, which is defined as the amount of lens power necessary to correct astigmatism. Astigmatism is a refractive error in which light rays do not have a single focus point on the retina, but rather multiple points before and afterr the retina, often caused by an irregularly shaped cornea. Another measurement can be axis 616, which is defined as the lens meridian that contains no cylinder power to correct astigmatism. Prism 617 can be measured, which is defined as the amount of lens power necessary to correct eye alignment deficiencies, such as double vision.

Then, in step 620, biometric measurements of the patient's head are taken. This can be accomplished by physically measuring the person, or through a series of photographs or video input of the person to calculate same. These measurements can include any one of, or a plurality of, the following, as further shown and described with reference to FIGS. 1, 2, and 3. Distance between the pupils 630 can be measured, which is defined as the distance between the center of each pupil 30, as shown in FIG. 2. Frontal curvature of the skull 631 can be measured, which is defined as the shape of the patient's face from temple to temple, and as further described in FIG. 3, element 31. Distance from the front of the temple to the back of the ear 622 can be measured, which is defined as the distance between the point of the temple closest to the face and the edge of the rear portion of the ear where it attaches to the head, as further described with reference to FIG. 1, element 22. The dimensions of the patient's eyes and nose 628 can be measured, which are defined as the measurement of the width of the patient's eyes, from corner to corner, and the measurement of the bridge of the nose across its vertical edges; the foregoing measurements are further described in FIGS. 2, 26 and 28, respectively.

A plurality of eyeglass frames is then exhibited 635. The eyeglass frames can be displayed in electronic form 632, defined as digital images, or physical form 634, defined as tangible samples of frames. A frame is selected from the exhibited frames 640.

The dimensions of the lens are matched to the selected eyeglass frame 650, wherein the frame dimensions are used to modify a lens to fit the frame. Alternatively, the shape of a lens is traced in step 645, which is defined as physically tracing the outer edge of the lens or doing so electronically. The trace is then used when matching the lens to the selected frame in step 650.

The collected data are then analyzed to generate a custom eyeglass frame 660. Said eyeglass frame is in electronic form which is transmitted to a 3D printer, which prints the eyeglass frame in step 670. The hinges may be modified electronically or digitally, based on the printed eyeglass frame in step 680. "Electronically" and "digitally," for the purposes of this disclosure, are used interchangeably and refer to the creation, representation, storage and processing of data, using a binary system or code of zeros and ones. Thereafter the hinges are printed using a 3D printer 690.

Figure 7:
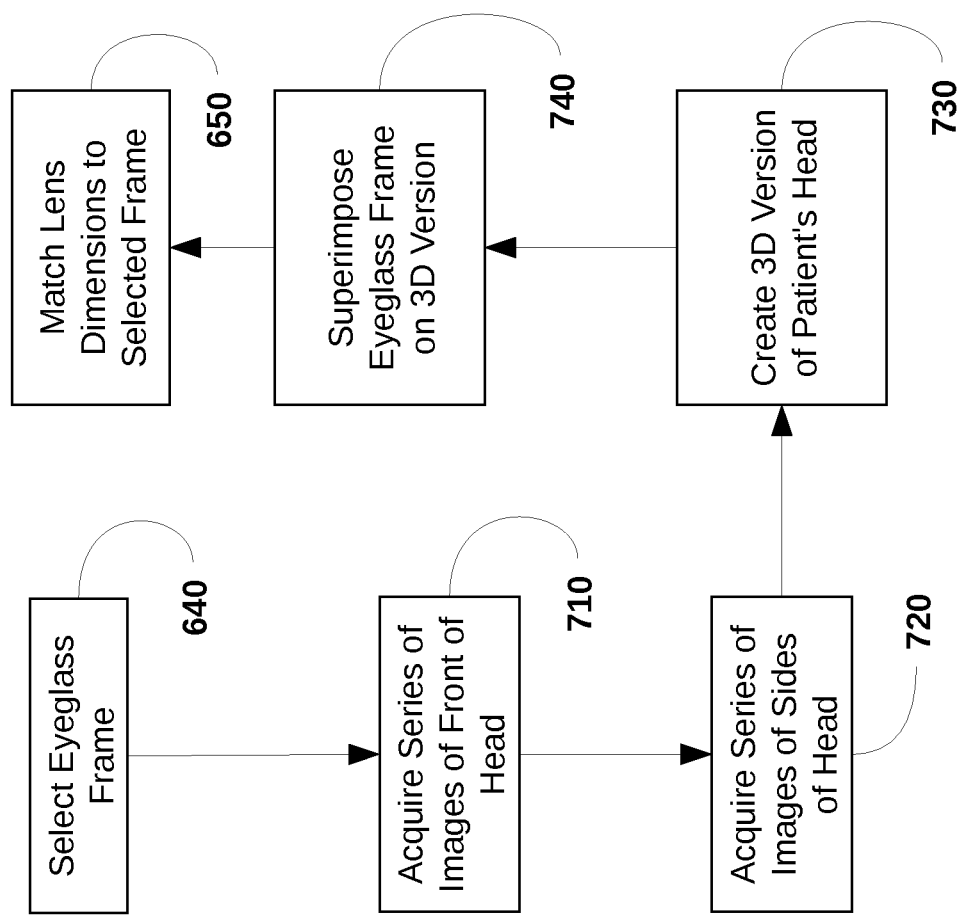
FIG. 7 shows a flowchart of a method of selecting an eyeglass frame based on imaging of a patient's head.

FIG. 7 shows a flowchart of a method of fabricating an eyeglass frame based on imaging of a patient's head. A series of images taken of the front of a patient are acquired in step 710. A series of images of the sides of a patients head are also acquired in step 720. Using the images, a 3D version of a patient's head is created in step 730. The selected eyeglass frame is superimposed on the 3D version of the patient's head in step 740.

Figure 8:
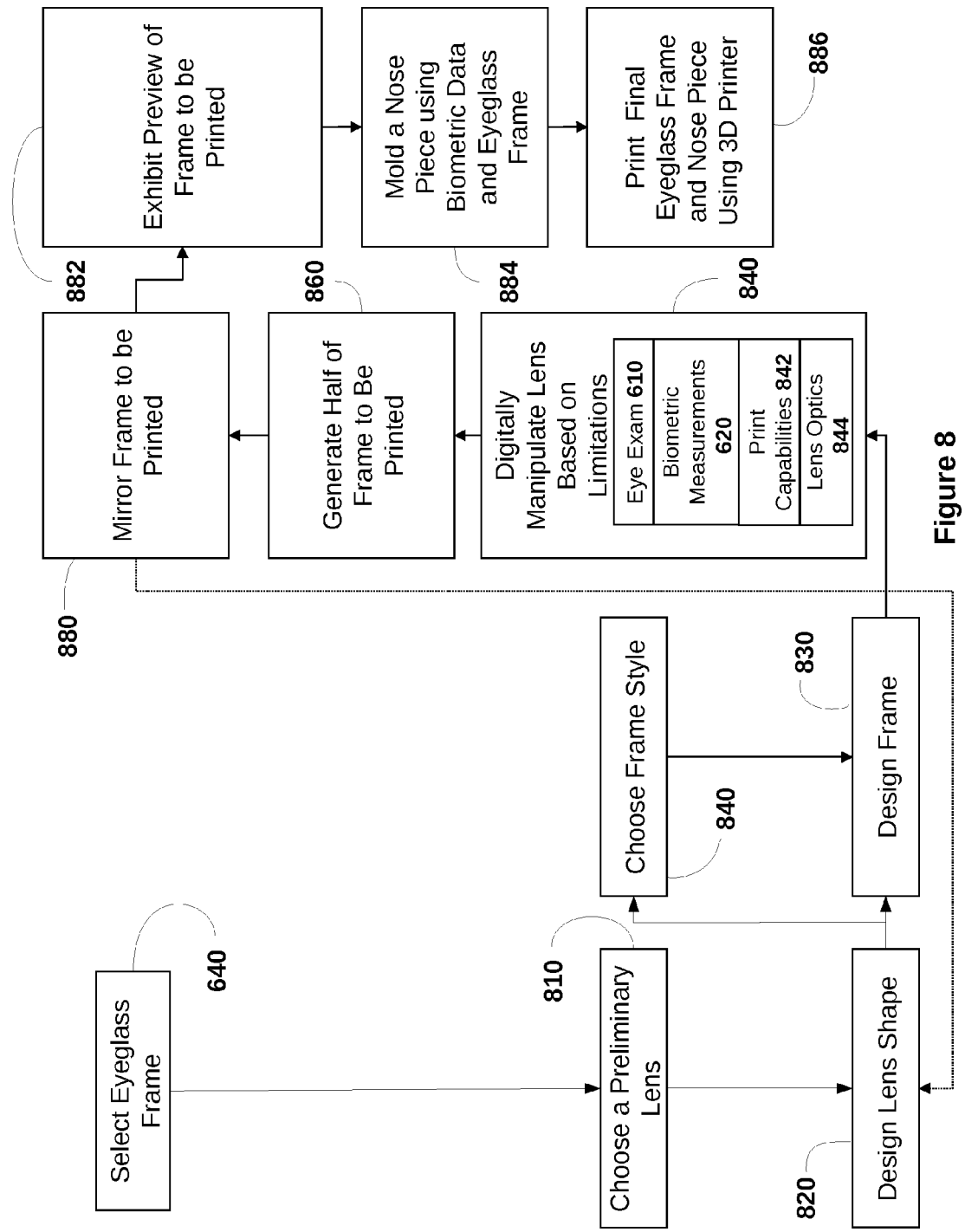
FIG. 8 shows a flowchart depicting the process of fabricating an eyeglass frame using a model based on a half frame version of an eyeglass frame and its mirror image.

FIG. 8 shows a flowchart of a method in which a preliminary lens outline is digitally shaped by the dimensions of the selected preliminary eyeglass frame to achieve a final lens design. After the selection of a preliminary eyeglass frame in step 640, wherein the frame has at least a distinct thickness between a top of the frame and a lens opening and a distinct lens opening width or height, a preliminary lens outline is determined in step 810. Said preliminary lens outline may be digitally shaped in the preliminary eyeglass frame design to achieve a lens design 820. The lens design may be used to modify the eyeglass frame design in step 830. Alternatively, the lens design may be used to determine the frame style in step 840, which in turn is used to modify the frame design in step 830. FIG. 4 further illustrates the process of using the lens dimensions 40 to modify the frame 42 to conform to such dimensions. The lens design is then digitally manipulated 840 based on the results of the eye examination in step 610, biometric measurements in step 620, print capabilities 842, and lens optics 844. Thereafter, the following steps are performed: half of the eyeglass frame to be printed is generated 860, a mirror image of the half frame is created 880, and a preview of the frame to be printed is displayed 882. FIG. 5 shows the complete version of an eyeglass frame 54 generated from an original half frame 50 and its mirror image 52. Based on the biometric data and eyeglass frame, a nose piece is generated 884. The final eyeglass frame and nose piece are then printed 886.

Figure 9:
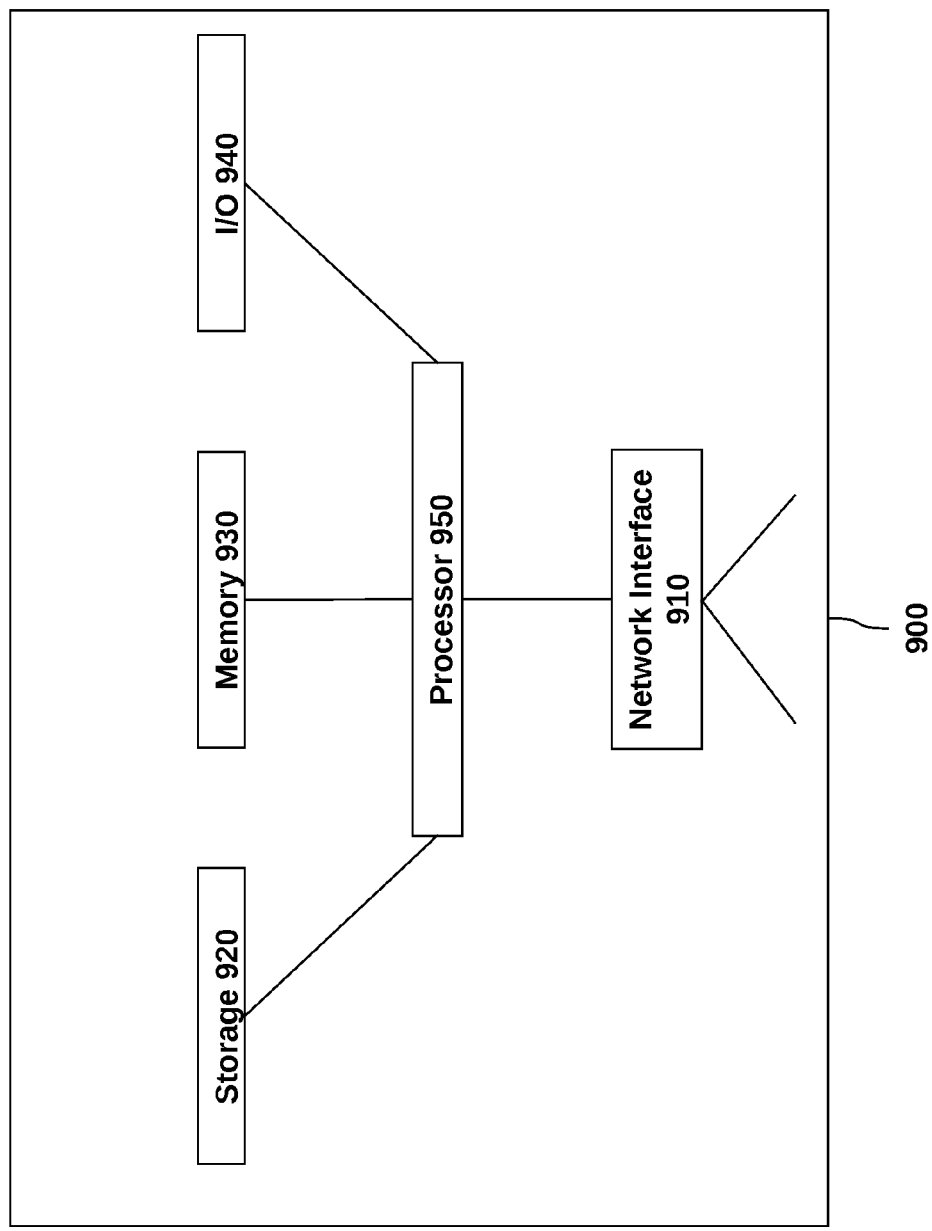
FIG. 9 shows a flowchart depicting the process of constructing an eyeglass frame using an electronic device to receive eyeglass specification data and transmitting it to a processor which performs a fit analysis.

FIG. 9 shows a high-level block diagram of a device that may be used to carry out the disclosed technology. Device 900 comprises a processor 950 that controls the overall operation of the computer by executing the device's program instructions which define such operation. The device's program instructions may be stored in a storage device 920 (e.g., magnetic disk, database) and loaded into memory 930, when execution of the console's program instructions is desired. Thus, the device's operation will be defined by the device's program instructions stored in memory 930 and/or storage 920, and the console will be controlled by processor 950 executing the console's program instructions. A device 900 also includes one or a plurality of input network interfaces for communicating with other devices via a network (e.g., the internet). The device 900 further includes an electrical input interface. A device 800 also includes one or more output network interfaces 910 for communicating with other devices. Device 900 also includes input/output 940 representing devices which allow for user interaction with a computer (e.g., display, keyboard, mouse, speakers, buttons, etc.). One skilled in the art will recognize that an implementation of an actual device will contain other components as well, and that FIG. 9 is a high level representation of some of the components of such a device for illustrative purposes. It should also be understood by one skilled in the art that the method and devices depicted in FIGS. 6 through 8 may be implemented on a device such as is shown in FIG. 9.

The invention claimed is:

1. A method of 3D printing eyeglasses comprising the steps of:
   (a) conducting a patient eye examination and determining said patient's optical specifications for vision correction, said optical specifications including at least two measurements selected from eye strength, refractive error, sphere, cylinder, axis and prism;
   (b) measuring biometric data of a head of said patient, including at least two of a distance between said patient's pupils, frontal curvature of patient's skull measured from temple to temple, distance from a front of said patient's temples to a back of said patient's ear, and dimensions and shape of said patient's eyes and bridge of the nose;

(c) selecting an eyeglass frame from a plurality of eyeglass frames, each representative of a different style, wherein a style is defined as having at least a distinct thickness between a top of said frame and a lens opening, left and right arms, a distinct bridge for a nose, and a distinct lens opening width or height compared to other styles exhibited;

(d) making a determination of lens dimensions which match said selection of said style of eyeglass frame;

(e) printing said selection of said style of eyeglass layer by layer with a three-dimensional printer, after first modifying a shape of at least two different and separate portions of said selection of said style of eyeglass frame, using said patient biometric data, a color of at least a part of said selection of said style of eyeglass frame, and adding at least one ornamental design selected by said patient to said selection of said style of eyeglass frame.

2. The method of claim 1, further including a step of modifying a shape of hinges for said selected style based on said modifying said shape of said eyeglass frame to match said printed eyeglass frame dimensions and printing such modified hinges.

3. The method of claim 1, wherein said step of exhibiting a plurality of eyeglass frames comprises a combination of exhibiting actual eyeglass frames and selectable electronically displayed versions thereof, showing examples of said eyeglass frames modifying a shape carried out during previous steps of said printing.

4. The method of claim 1, further including a step of taking a series of digital images of said patient's head, comprising images of at least the face and sides of said patient's head and, before said step of printing, modifying said shape of said at least two different and separate portions of said selection of said style of eyeglass frame, based on a superposition of said selection of said style of eyeglass frame on said digital images.

5. The method of claim 4, wherein a three-dimensional version of said patient's head is generated from said series of digital images, using said patient biometric data.

6. The method of claim 5, wherein said left and right arms of said selection of said style of eyeglass frame are generated by form-fitting two curves and combining said two curves, one of said curves sized using the shape and size of one of said left and right arms, and the second of said curves having the shape of one of said patient's temples determined using said patient's biometric data and said three-dimensional version of patient's head.

7. The method of claim 1, wherein a single outline of at least one said lens is traced, and the dimensions of such lens are used to modify the shape of the selected eyeglass frame.

8. The method of claim 7, wherein said traced outline of said lens is used to limit modification to said style of eyeglass frame, such that when said modifying of a shape of at least two different and separate portions of said selection of said style of eyeglass frame, parts of said eyeglass which hold said lens, are held constant.

9. A method for custom designing or fitting 3D printed eyeglasses, said method comprising the steps of:

(a) conducting a patient eye examination and determining said patient's optical specifications for vision correction, said optical specifications including at least two of said patient's eye strength, refractive error, sphere, cylinder, axis, and prism;

(b) measuring biometric data of a head of said patient, including at least two of a distance between said patient's pupils, frontal curvature of patient's skull measured from temple to temple, the distance from a front of said patient's temples to a back of said patient's ear, and dimensions and shape of said patient's eyes, nose and ears;

(c) choosing a preliminary lens outline based on said patient biometric data and said optical specifications, wherein said preliminary lens outline is digitally shaped in a preliminary eyeglass frame design to achieve a final lens design, said preliminary eyeglass frame design having at least a distinct thickness between a top of said frame and a lens opening, and a distinct lens opening width or height;

(d) generating one-half of a bridge portion of a preliminary eyeglass frame design and further generating a mirror image of said one-half of a nose bridge portion and a mirror image of said preliminary eyeglass frame design;

(e) modifying and final shaping of said preliminary eyeglass frame design using said final lens design, said nose bridge portion and said mirror images generated in step (d) to create a final frame design;

(f) molding a nose piece, using said patient biometric data and said final frame design; and (g) printing said final frame design as modified, and said nose piece layer by layer, using a three-dimensional printer, after first modifying a color of at least a part of said final frame design and adding at least one design to said final frame design.

10. The method of claim 9, wherein said final frame design includes left and right arms, said left and right arms being generated using said patient biometric data.

11. The method of claim 10, further including a step of splitting said final frame design from said left and right arms, and using a liquid resin printer to print three-dimensional replicas of said final frame design and said left and right arms to scale.

12. The method of claim 9, further including a step of using said patient biometric data and said optical specifications to generate a second lens for assembly into said final frame design.

13. The method of claim 9, further including a step of modifying said final frame design to fit said patient's frontal facial curvature.

14. The method of claim 9, further including a step of modifying a shape of hinges between left and/or right arms of said final design to match said printed final frame design.

15. A custom eyeglass design and fitting system, comprising:

a processor;

a device, which receives and electronically stores data, information and instructions; that instructs said processor to perform acts for enabling the fabrication of a custom-fit or custom-designed eyeglass frame, using data and information retrievable from said device, said data and information including:

(i) patient eye examination data, wherein said patient eye examination data includes patient's optical specifications for vision corrections, said optical specifications including at least two of said patient's eye strength, refractive error, sphere, cylinder, axis, prism, and add;

(ii) patient biometric data, including at least two of a distance between said patient's pupils, frontal curvature of said patient's skull measured from temple to temple, distance from a front of said patient's temples to a back of said patient's ear, and dimensions and shape of said patient's eyes, nose, eye sockets and ears; and
(iii) preliminary eyeglass frame size data, wherein a preliminary eyeglass frame design includes a frame portion defining two lens receiving openings, said frame portion further supporting left and right arms, the arms located on opposite distal ends of said frame portion, and wherein said preliminary eyeglass frame size data include lens opening width and height, bridge width, temple length and total width;

an input mechanism for transmitting said data and information to said processor, wherein said processor implements a fit analysis, using said preliminary eyeglass frame design size data, said patient biometric data and said optical specifications to alter said preliminary eyeglass frame design to generate a custom fit eyeglass frame for said patient; and a three-dimensional printer functionally connected to said processor for printing said custom-fit eyeglass frame layer by layer.

16. The system of claim 15, wherein said processor executes instructions for generating an outline of a preliminary lens, using said patient biometric data and said optical specifications, wherein said processor further implements instructions that determine the vertical and outward shape of said outline of said preliminary lens in said preliminary eyeglass frame design.

17. The system of claim 15 wherein said processor executes instructions for generating (a) one-half of a bridge portion of said preliminary eyeglass frame design, (b) a mirror image of said one-half of a nose bridge portion, and (c) a mirror image of said preliminary eyeglass frame design, wherein said processor uses said patient biometric data, said optical specifications and said preliminary eyeglass frame size data to generate a final eyeglass frame design, a final lens design and a final nose bridge design.

18. The system of claim 17, wherein said processor uses said final eyeglass frame design and said patient biometric data to mold a nose piece for said final eyeglass frame design.

19. The system of claim 18, wherein said nose piece is printed layer by layer, using said three-dimensional printer, wherein said nose piece is assembled onto said final eyeglass frame design after printing.

* * * * *